US011116493B2

(12) United States Patent
Palese et al.

(10) Patent No.: US 11,116,493 B2
(45) Date of Patent: Sep. 14, 2021

(54) KNOTLESS LATERAL ROW IMPLANT

(71) Applicant: Biomet Manufacturing, LLC, Warsaw, IN (US)

(72) Inventors: Christopher M. Palese, Warsaw, IN (US); Jacy C. Hoeppner, Warsaw, IN (US); Jason D. Meridew, Warsaw, IN (US); Kevin T. Stone, Winona Lake, IN (US)

(73) Assignee: Biomet Manufacturing, LLC, Warsaw, IN (US)

( * ) Notice: Subject to any disclaimer, the term of this patent is extended or adjusted under 35 U.S.C. 154(b) by 226 days.

(21) Appl. No.: 15/987,380

(22) Filed: May 23, 2018

(65) Prior Publication Data

US 2018/0338755 A1 Nov. 29, 2018

Related U.S. Application Data

(60) Provisional application No. 62/510,963, filed on May 25, 2017.

(51) Int. Cl.
*A61B 17/04* (2006.01)
(52) U.S. Cl.
CPC .... *A61B 17/0401* (2013.01); *A61B 2017/044* (2013.01); *A61B 2017/0409* (2013.01); *A61B 2017/0414* (2013.01); *A61B 2017/0438* (2013.01); *A61B 2017/0445* (2013.01)
(58) Field of Classification Search
CPC ........ A61B 17/0401; A61B 2017/0409; A61B 17/0414; A61B 17/044; A61B 17/0441; A61B 17/0445
See application file for complete search history.

(56) References Cited

U.S. PATENT DOCUMENTS

| 2006/0235413 | A1* | 10/2006 | Denham | A61B 17/0401 606/232 |
| 2009/0299386 | A1* | 12/2009 | Meridew | A61F 2/0811 606/151 |
| 2013/0144334 | A1* | 6/2013 | Bouduban | A61B 17/0401 606/232 |

* cited by examiner

*Primary Examiner* — Todd J Scherbel
(74) *Attorney, Agent, or Firm* — Schwegman Lundberg & Woessner, P.A.

(57) ABSTRACT

An anchoring system includes an anchor including an anchor body and a distal member located at a distal end of the anchor body, the distal member having a suture receiving aperture; and an implant delivery device, comprising: a cannulated outer shaft, the cannulated outer shaft configured to engage a proximal end of the anchor body for driving the anchor into a bore; and an inner shaft slidably received in the cannulated outer shaft, wherein a distal end of the inner shaft is extendable distally beyond a distal end section of the cannulated outer shaft such that, when the cannulated outer shaft is engaging the proximal end of the anchor body, the distal end of the inner shaft is extendable through the anchor body to a distance beyond the distal end of the anchor body to engage a suture located within the suture receiving aperture, wherein the anchoring system is configured such that the suture can be tensioned at a location within the bore distal from the anchor body before the anchor body is implanted within the bore.

13 Claims, 10 Drawing Sheets

KNOTLESS LATERAL ROW IMPLANT

CLAIM OF PRIORITY

This application claims the benefit of U.S. Provisional Patent Application Ser. No. 62/510,963, filed on May 25, 2017, the benefit of priority of which is claimed hereby, and which is incorporated by reference herein in its entirety.

FIELD OF THE DISCLOSURE

The present subject matter relates to securing a suture to a bore, such as in a portion of bone.

BACKGROUND

In the human body, tissue can require repair. For example, a tear in a rotator cuff can require surgical repair of the rotator cuff. Surgeons often use suture anchors to secure bone and tissue in place during a surgical procedure. A suture is connected to the anchor, which is typically implanted in bone.

OVERVIEW

In a first example, an anchoring system can include an anchor including an anchor body and a distal member located at a distal end of the anchor body, the distal member having a suture receiving aperture; and an implant delivery device, comprising: a cannulated outer shaft, the cannulated outer shaft configured to engage a proximal end of the anchor body for driving the anchor into a bore; and an inner shaft slidably received in the cannulated outer shaft, wherein a distal end of the inner shaft is extendable distally beyond a distal end section of the cannulated outer shaft such that, when the cannulated outer shaft is engaging the proximal end of the anchor body, the distal end of the inner shaft is extendable through the anchor body to a distance beyond the distal end of the anchor body to engage a suture located within the suture receiving aperture, wherein the anchoring system is configured such that the suture can be tensioned at a location within the bore distal from the anchor body before the anchor body is implanted within the bore.

In example 2, the anchoring system of example 1 can include a configuration such that a suture located in the suture receiving aperture is driven distally beyond the distal member.

In example 3, the anchoring system of example 2 can include the suture receiving aperture including a pair of openings on opposing sides of the distal member defining an eyelet.

In example 4, the anchoring system of any of examples 2 or 3 can include the inner shaft including a fork on the distal end of the inner shaft, the fork configured to hold the suture as the distal end of the inner shaft is extended beyond the distal end of the distal member.

In example 5, the anchoring system of example 4 can include the fork being a two-pronged fork.

In example 6, the anchoring system of any of examples 2-5 can include the anchoring system being configured so that the suture is at a proper location to be tensioned when the distal end of the inner shaft is on a bottom surface of the bore and holding the suture at a distal positon of the bore.

In example 7, the anchoring system of any of examples 1-6 can include the suture receiving aperture including a slot in the distal member.

In example 8, the anchoring system of example 7 can include the slot being an L-shaped slot with an opening on a side of the distal member defining a first leg of the L-shaped slot and a longitudinally running slot in the distal member defining a second leg of the L-shaped slot.

In example 9, the anchoring system of example 8 can include a distal end of the distal member being closed and when the inner shaft is extended at least a portion of the inner shaft covers the opening on the side of the distal member so as to secure the suture within the distal member.

In example 10, the anchoring system of example 9 can include the anchoring system being configured such that the suture located in the suture receiving aperture is not driven distally beyond the distal member.

In example 11, the anchoring system of any of examples 1-10 can include the distal member being rotatable relative to the anchor body.

In example 12, the anchoring system of any of examples 1-11 can include anchor body including a threaded outer surface.

In example 13, the anchoring system of example 12 can include the distal end section of the cannulated outer shaft engaging the proximal end of the anchor body for rotating the anchor body with the cannulated outer shaft.

In example 14, a method for securing a suture to a bore can include: mounting an anchor to an implant deliver device, the anchor including an anchor body and a distal member located at a distal end of the anchor body; loading a suture into the distal member of the anchor; positioning a portion of the suture distally past a distal end of the anchor body; positioning the anchor at a bore so that the portion of the suture distally past the distal end of the anchor body is located at or near a bottom of the bore while the anchor by is above the bore; tensioning the suture; and driving the anchor body into the bore to secure the suture.

In Example 15, the method of example 14 can include the distal member including a suture receiving aperture and the suture loaded through the suture receiving aperture.

In example 16, the method of any of examples 14-15 can include the implant delivery device includes a cannulated outer shaft, the cannulated outer shaft including a distal end configured to engage a proximal end of the anchor body for driving the anchor into a bore; and an inner shaft slidably received in the cannulated outer shaft, wherein a distal end of the inner shaft is extendable distally beyond the distal end of the cannulated outer shaft such that, when the distal end of the cannulated outer shaft is engaging the proximal end of the anchor body, the distal end of the inner shaft is extendable through the anchor body to a distance beyond the distal end of the anchor body to engage the suture.

In example 17, the method of example 16 can include the anchoring system being configured such that the suture is driven distally beyond the distal member before the anchor is positioned at the bore.

In example 18, the method of example 17 can include the inner shaft including a fork on the distal end of the inner shaft, the fork configured to hold the suture as the distal end of the inner shaft is extended beyond the distal end of the distal member.

In example 19, the method of any of examples 14-18 can include the distal member including a slot as a suture receiving aperture, wherein the slot is an L-shaped slot with an opening on a side of the distal member defining a first leg of the L-shaped slot and a longitudinally running slot in the distal member defining a second leg of the L-shaped slot.

In example 20, the method of example 19 can include a distal end of the distal member being closed and when the inner shaft is extended at least a portion of the inner shaft covers the opening on the side of the distal member so as to secure the suture within the distal member.

These examples can be combined in any permutation or combination. This overview is intended to provide an overview of subject matter of the present patent application. It is not intended to provide an exclusive or exhaustive explanation of the invention. The detailed description is included to provide further information about the present patent application.

BRIEF DESCRIPTION OF THE DRAWINGS

Corresponding reference characters indicate corresponding parts throughout the several views. Elements in the drawings are not necessarily drawn to scale. The configurations shown in the drawings are merely examples, and should not be construed as limiting the scope of the invention in any manner.

DETAILED DESCRIPTION

During a surgical process, such as a rotator cuff repair surgery, a surgeon can prepare one or more bores in a bone. The surgeon can affix sutures to the bone at each bore. For each hole, the surgeon can deploy an anchor with an anchor body into the bore, which can secure the suture between the threads of the anchor body and the wall of the bore. The devices and methods discussed herein pertain to the anchor, the elements used in an implant delivery device that can deploy the anchor, and a method of deploying the anchor.

Figure 1:
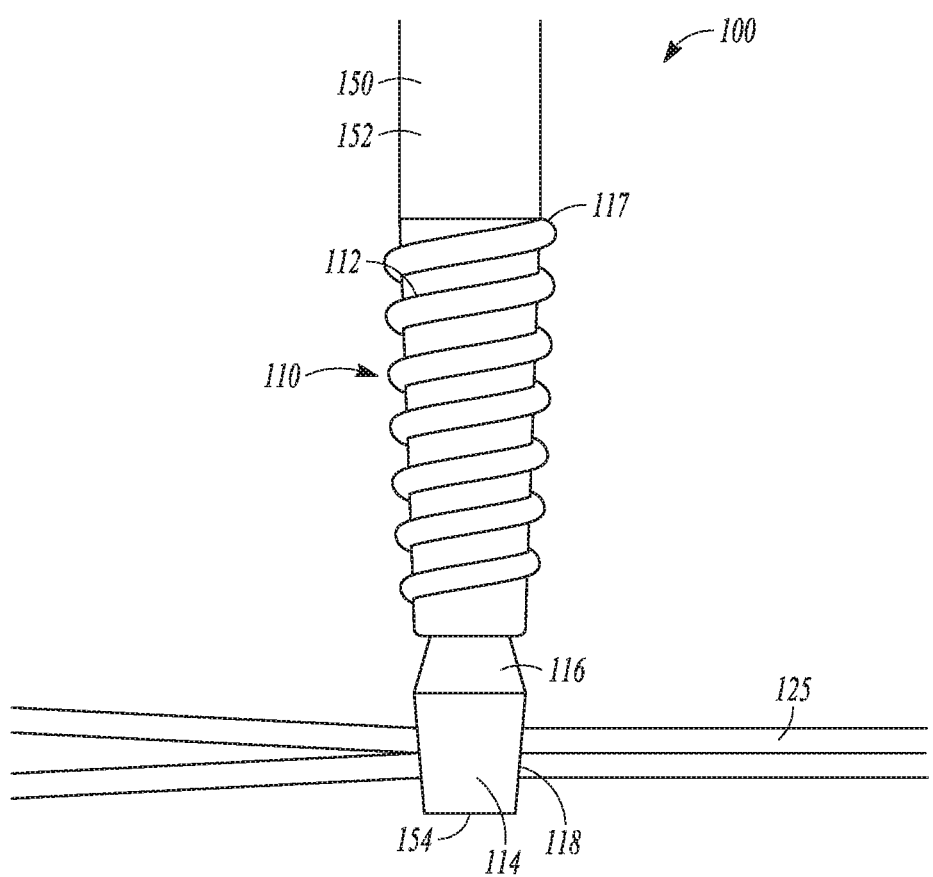
FIG. 1 shows a perspective view of an anchoring system, according to one embodiment.

FIG. 1 shows a perspective view of an anchoring system 100, according to one embodiment. The anchoring system 100 can include an anchor 110 including an anchor body 112 and a distal member 114 located at a distal end 116 of the anchor body 112. The distal member 114 can include a suture receiving aperture 118 to receive one or more suture 125. The distal member 114 can be rotatable relative to the anchor body 112.

The anchoring system 100 can further include an implant delivery device 150. The implant delivery device 150 can include a cannulated outer shaft 152 and an inner shaft 154 slidably received in the cannulated outer shaft 152.

Figure 2:
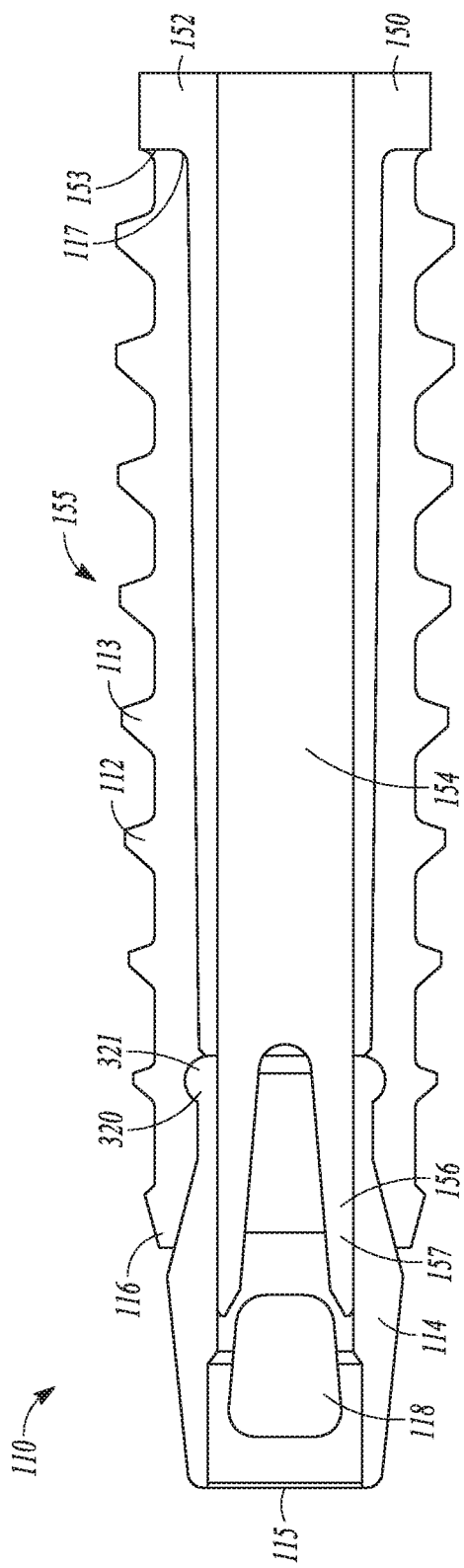
FIG. 2 shows a cross section view of portions of the anchoring system of FIG. 1, according to one embodiment.

Referring now also to FIG. 2, which shows a cross section view of portions of the anchoring system 100 showing further details, the anchor body 112 can include a cannulated body defining an inner bore and a threaded outer surface 113. Here, the cannulated outer shaft 152 can include a distal end section 155 configured to engage a proximal end 117 of the anchor body 112 for rotatably driving the anchor body 112 into a bore via the threaded outer surface 113. Since the distal member 114 is rotatable relative to the anchor body 112, the distal member 114 does not rotate as the anchor body 112 is threadably implanted. The cannulated outer shaft 152 includes a shoulder 153 on the distal end section 155 which can abut the proximal end 117 of the anchor body 112 when the anchor body 112 is fully seated on the implant delivery device 150.

As will be explained in further detail below, a distal end 156 of the inner shaft 154 is extendable distally beyond the distal end section 155 of the cannulated outer shaft 152 such that, when the distal end section 155 of the cannulated outer shaft 152 is engaging the proximal end 117 of the anchor body 112, the distal end 156 of the inner shaft 154 is extendable through the anchor body 112 to a distance beyond the distal end 116 of the anchor body 112 to engage the suture 125 located within the suture receiving aperture 118. Thus, the anchoring system 100 is configured such that the suture 125 can be tensioned at a location within a bore distal from the anchor body 112 before the anchor body 112 is implanted within the bore. This allows for better and easier implants and allows a surgeon to have the desired tension in the suture before the anchor is implanted.

In this example, the inner shaft 154 can include a fork 157, such as a two-pronged fork, on the distal end 156 of the inner shaft 154. The fork 157 can be configured to hold the suture 125 as the distal end 156 of the inner shaft 154 is extended beyond a distal end 115 of the distal member 114.

Figure 3:
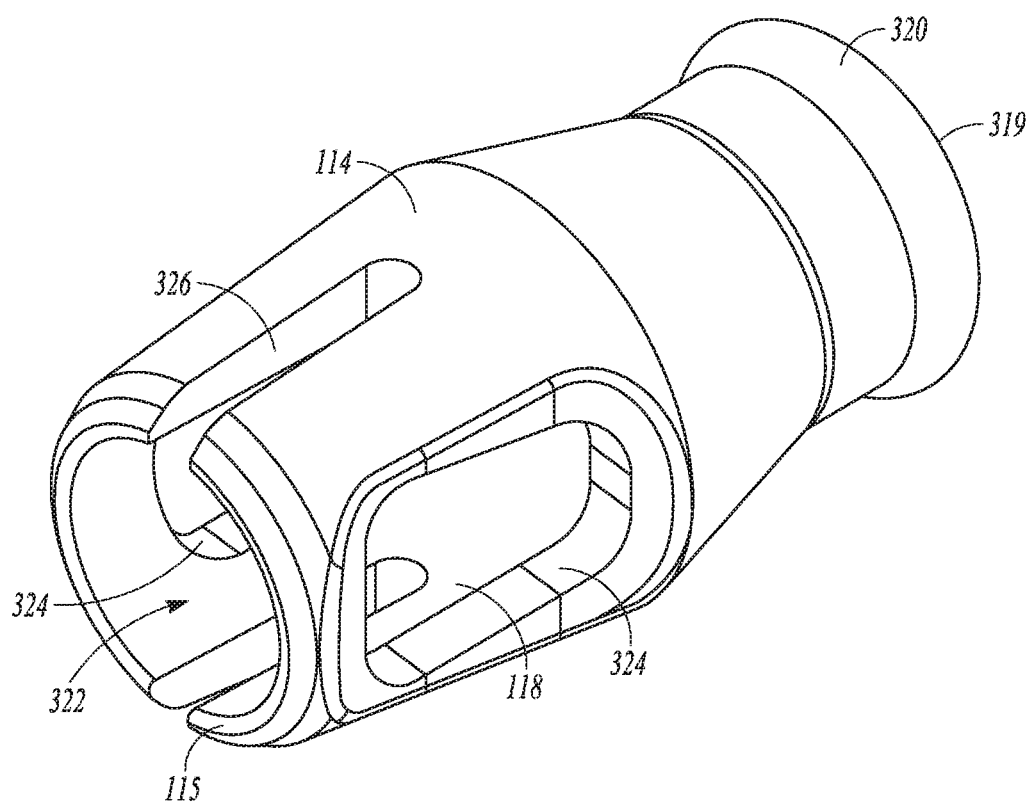
FIG. 3 shows a perspective view of a distal member of an anchor, according to one embodiment.

FIG. 3 shows a perspective view of the distal member 114 of the anchor 110, according to one embodiment. In this example, the suture receiving aperture 118 of the distal member 114 includes a pair of openings 324 on opposing sides of the distal member 114 defining an eyelet to receive the suture therethrough. The distal member 114 includes a bore 322 extending from the distal end to a proximal end 319. A lip 320 at proximal end 319 can be fitted into an indent 321 (FIG. 2) of the anchor body 112 to hold the distal member 114 in place. One or more slots 326 can extend longitudinally through the distal member 114 to allow the distal bore 322 to be flexible while the inner shaft 154 is deployed engaging the sutures 125 from the aperture 118.

Figure 4:
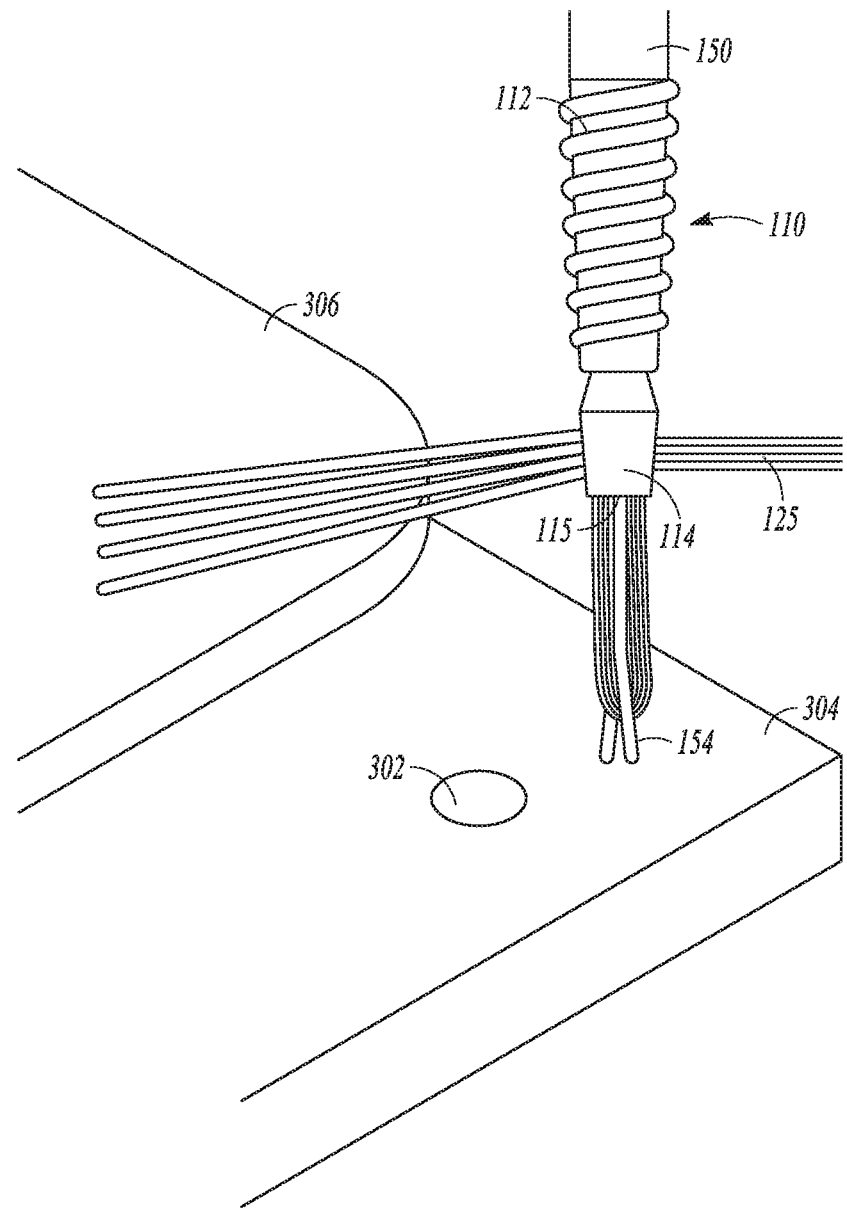
FIG. 4 shows a perspective view of the anchoring system of FIG. 1, according to one embodiment.

FIGS. 1 and 4, 5, 6, show an example use of the anchoring system 100. In FIG. 1, the one or more sutures 125 are loaded through the suture receiving aperture 118. In FIG. 4, a bore 302 has been prepared in a bone 304 to receive the anchor 110 to attach a tissue 306 to the bone 304. The inner shaft 154 is deployed such that it engages the sutures 125 within the suture receiving aperture 118 and then holds and drives the sutures 125 out distally past the distal end 115 of the distal member 114.

Figure 5:
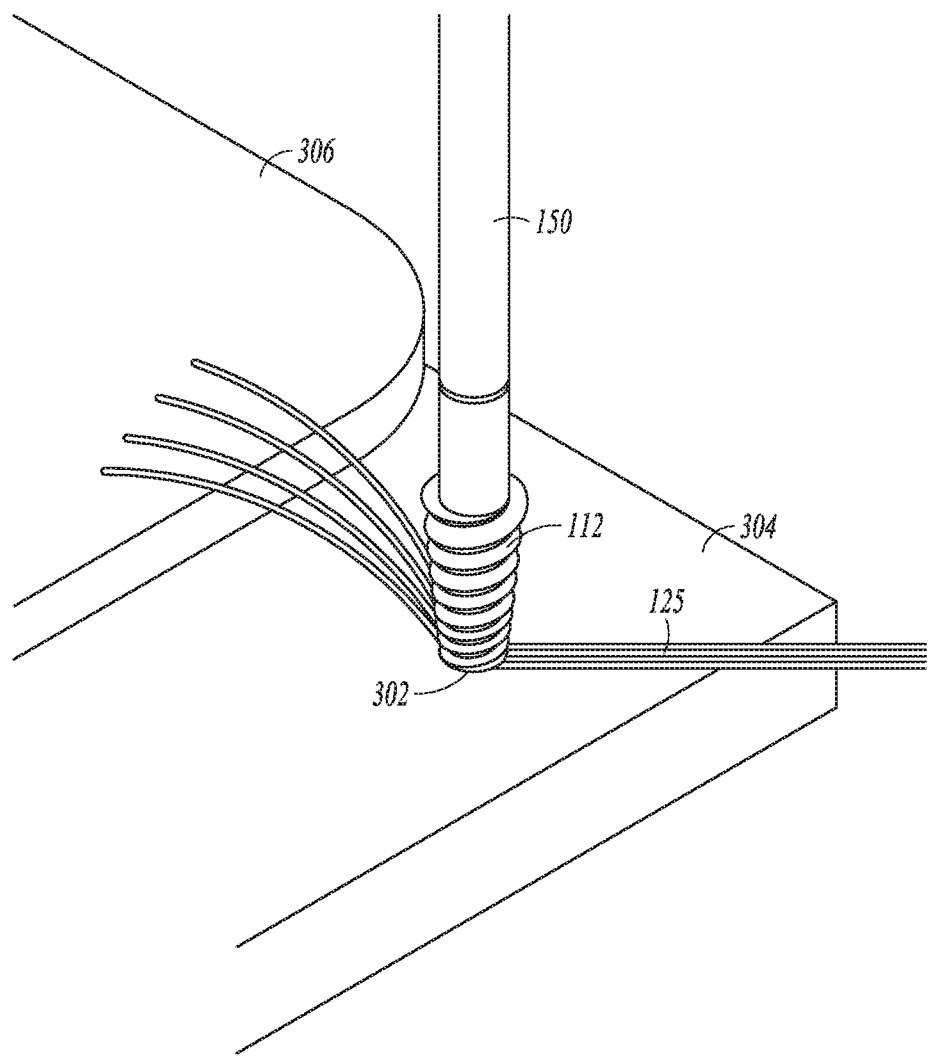
FIG. 5 shows a perspective view of the anchoring system of FIG. 1, according to one embodiment.

In FIG. 5 the inner shaft 154 has been introduced into the bore 302 with the inner shaft 154 still deployed as in FIG. 4 until the distal end of the inner shaft 154 bottoms out on a bottom surface of the bore 302. Anchor body 112 is positioned at the top surface of the bore 302, while the sutures 125 at the end of the inner shaft 154 are located near or at the bottom of the bore 302. The sutures 125 can then be tensioned as desired. Thus, the anchoring system 100 is configured so that the sutures are at a proper location within the bore 302 so as to be tensioned before the anchor is implanted and when the distal end of the inner shaft is on a bottom surface of the bore and holding the sutures at a distal location within the bore.

Figure 6:
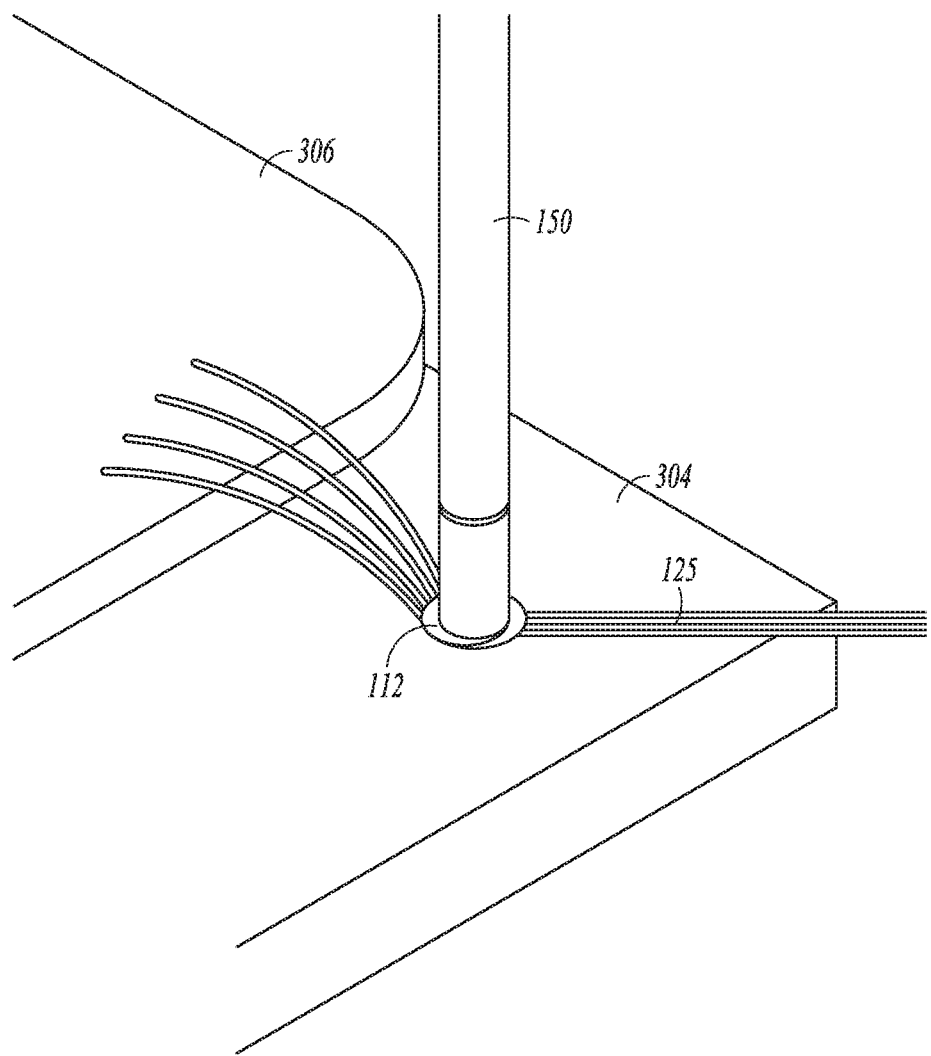
FIG. 6 shows a perspective view of the anchoring system of FIG. 1, according to one embodiment.

Once, the sutures 125 are properly tensioned, the implant delivery device 150 can rotatably implant the anchor body 112 until the distal end of the anchor body is flush with the bone 304 surface, as shown in FIG. 6. Thus, the sutures 125 are captured between the bore wall and the outer surface of the anchor body 112. The implant delivery device is then removed.

Figure 7:
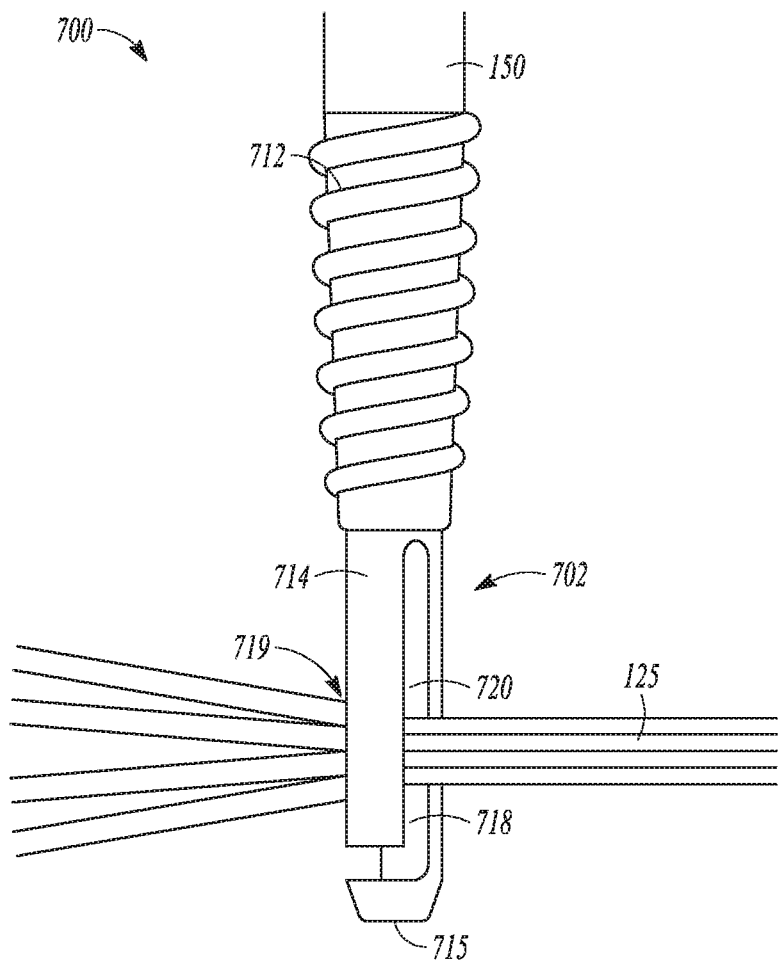
FIG. 7 shows a perspective view of an anchoring system, according to one embodiment.

FIG. 7 shows a perspective view of an anchoring system 700, according to one embodiment. System 700 includes many features similar to system 100 discussed above and certain details will be omitted. Here, the anchoring system 700 can include an anchor 702 to be implanted by the implant delivery device 150.

The anchor 702 includes an anchor body 712 with a threaded outer surface, similar to anchor body 112, discussed above. The anchor further includes a distal member 714. Instead of an eyelet-like aperture, the suture receiving aperture of distal member 714 can include a slot 718 in the distal member 714. Slot 718 can include an L-shaped slot with an opening 719 on a side of the distal member defining a first leg of the L-shaped slot and a longitudinally running slot 720 in the distal member defining a second leg of the L-shaped slot. The open design allows for quick loading of the suture 125 which can be slipped through the opening 719 into the longitudinal slot 720.

Figure 8:
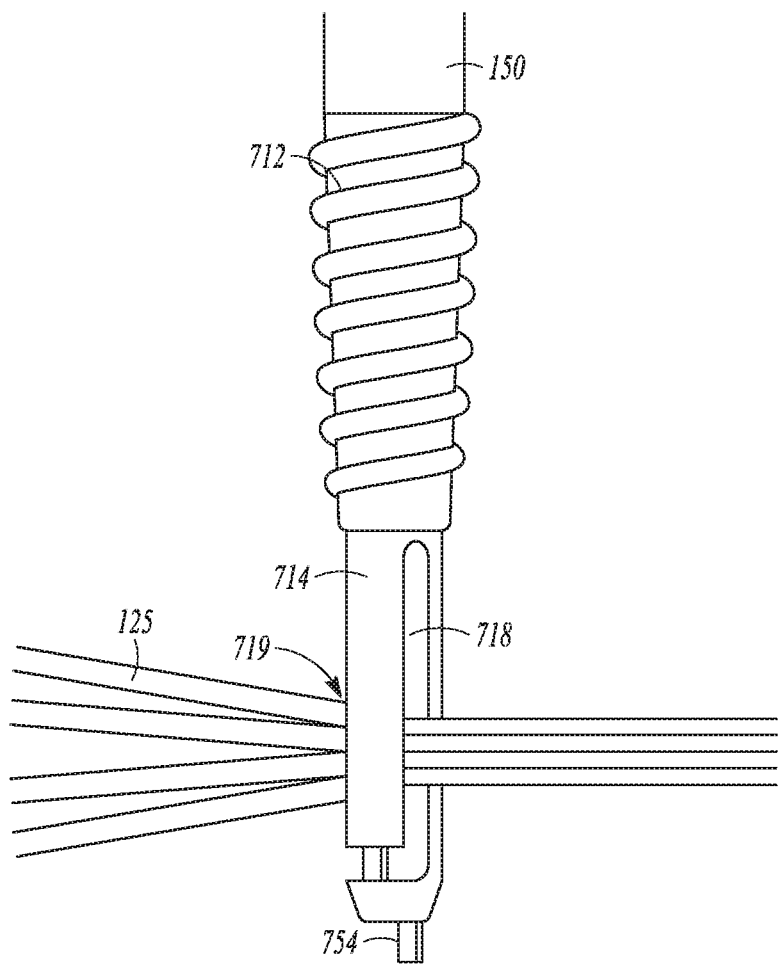
FIG. 8 shows a perspective view of the anchoring system of FIG. 7, according to one embodiment.

Referring now also to FIG. 8, a distal end 715 of the distal member 714 is closed such that when the inner shaft 754 is extended into the distal member 714, at least a portion of the inner shaft 754 covers the opening 719 on the side of the distal member 719. This secures the suture 125 within the distal member 714 at or near a distal portion of the distal member 714. The distal member 714 is longer than the distal member 114 discussed above, and the suture is now positioned such that it is not necessary to drive the suture distally beyond the distal member 714.

Figure 9:
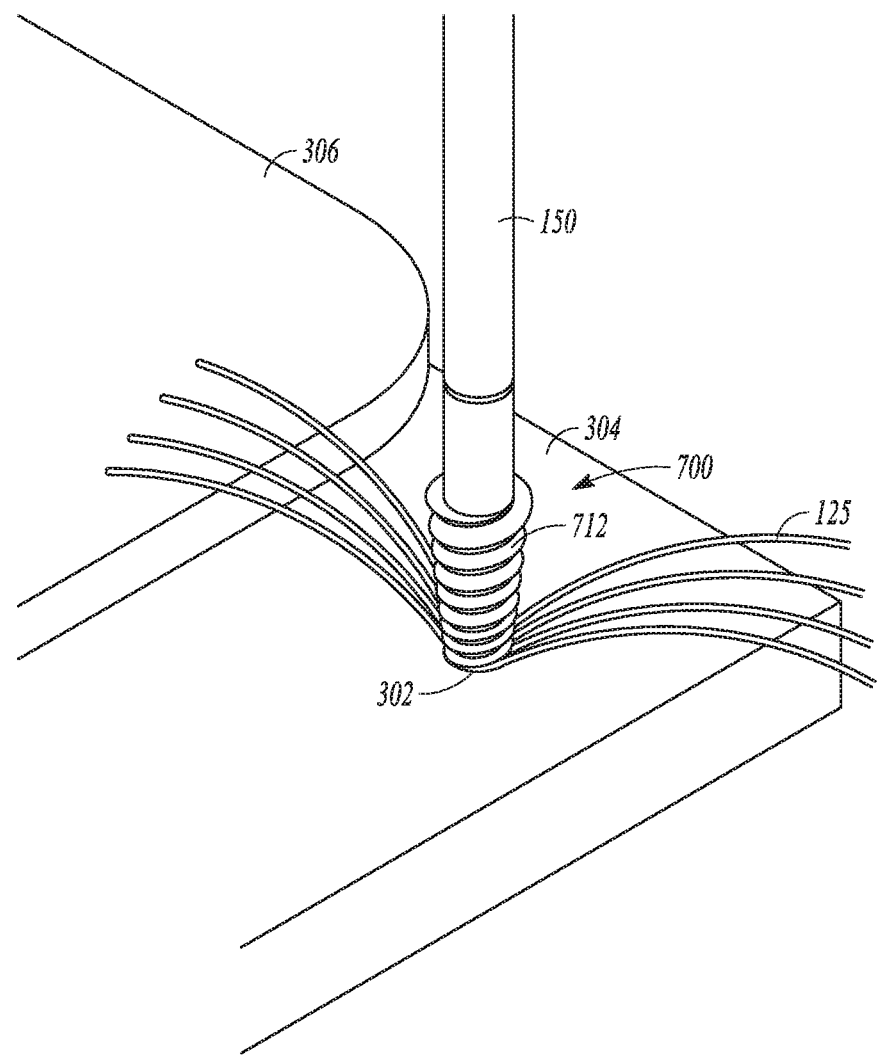
FIG. 9 shows a perspective view of the anchoring system of FIG. 7, according to one embodiment.
Figure 10:
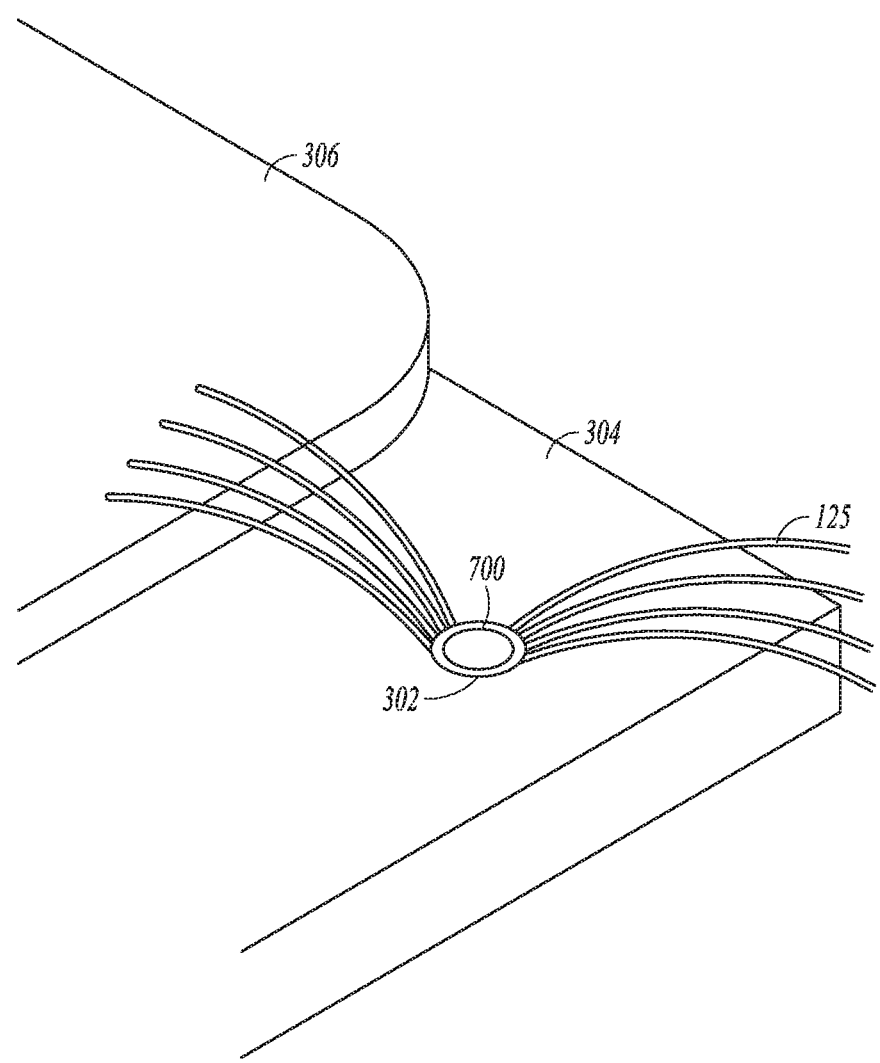
FIG. 10 shows a perspective view of an implanted anchor, according to one embodiment.

In FIG. 9, the anchor 700 is pushed into the bore 302 until the distal end of the anchor body 712 is at the top surface of the bore 302. At that time the sutures 125 in the distal member 714 are at or near a bottom of the bore 302. The sutures 125 can then be tensioned and the anchor body 712 is driven into the bore until it is fully seated and then the implant delivery device 150 is removed, as shown in FIG. 10.

In an example, the anchor body 712 is cannulated and the distal member 714 at least partially enters the cannulated anchor body 712 as the anchor body 712 is driven into the bore 302 over the distal member 714.

Again, for the anchoring systems discussed herein, the systems are configured such that a suture can be tensioned at a location within the bore distal from the anchor body before the anchor body is implanted within the bore. This allows for better and easier implants and allows a surgeon to have the desired tension in the suture with the suture in the desired location within the bore before the anchor is implanted. Moreover, the system allows for the ability to tension and fixate lateral row anchors without needing knots in a rotator cuff repair.

Additional Notes

The above detailed description includes references to the accompanying drawings, which form a part of the detailed description. The drawings show, by way of illustration, specific embodiments in which the invention can be practiced. These embodiments are also referred to herein as "examples." Such examples can include elements in addition to those shown or described. However, the present inventors also contemplate examples in which only those elements shown or described are provided. Moreover, the present inventors also contemplate examples using any combination or permutation of those elements shown or described (or one or more aspects thereof), either with respect to a particular example (or one or more aspects thereof), or with respect to other examples (or one or more aspects thereof) shown or described herein.

All publications, patents, and patent documents referred to in this document are incorporated by reference herein in their entirety, as though individually incorporated by reference. In the event of inconsistent usages between this document and those documents so incorporated by reference, the usage in the incorporated reference(s) should be considered supplementary to that of this document; for irreconcilable inconsistencies, the usage in this document controls.

In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In the appended claims, the terms "including" and "in which" are used as the plain-English equivalents of the respective terms "comprising" and "wherein." Also, in the following claims, the terms "including" and "comprising" are open-ended, that is, a system, device, article, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

What is claimed is:

1. An anchoring system, comprising:
    an anchor including an anchor body and a distal member located at a distal end of the anchor body, the distal member having a suture receiving aperture; and
    an implant delivery device, comprising:
    a cannulated outer shaft, the cannulated outer shaft configured to engage a proximal end of the anchor body for driving the anchor into a bore; and
    an inner shaft slidably received in the cannulated outer shaft, wherein a distal end of the inner shaft is extendable distally beyond a distal end section of the cannulated outer shaft such that, when the cannulated outer shaft is engaging the proximal end of the anchor body, the distal end of the inner shaft is extendable through the anchor body to a distance beyond the distal end of the anchor body to engage a suture located within the suture receiving aperture, wherein the anchoring system is configured such that the suture can be tensioned at a location within the bore distal from the anchor body before the anchor body is implanted within the bore, wherein the distal member includes slots longitudinally extending along the distal member and open at a distal end of the distal member and separate from the suture receiving aperture, wherein the slots extend up the distal member so as to be at least partially co-extensive along a cross-section perpendicular to a longitudinal axis of the distal member with the suture receiving aperture.

2. The anchoring system of claim 1, wherein the anchoring system is configured such that a suture located in the suture receiving aperture is driven distally beyond the distal member.

3. The anchoring system of claim 2, wherein the suture receiving aperture includes a pair of openings on opposing sides of the distal member defining an eyelet.

4. The anchoring system of claim 2, wherein the inner shaft includes a fork on the distal end of the inner shaft, the fork configured to hold the suture as the distal end of the inner shaft is extended beyond the distal end of the distal member.

5. The anchoring system of claim 4, wherein the fork is a two-pronged fork.

6. The anchoring system of claim 2, wherein the anchoring system is configured so that the suture is at a proper location to be tensioned when the distal end of the inner shaft is on a bottom surface of the bore and holding the suture at a distal position of the bore.

7. The anchoring system of claim 1, wherein the distal member is rotatable relative to the anchor body.

8. The anchoring system of claim 1, wherein the anchor body includes a threaded outer surface.

9. The anchoring system of claim 8, wherein the distal end section of the cannulated outer shaft can engage the proximal end of the anchor body for rotating the anchor body with the cannulated outer shaft.

10. The anchoring system of claim 1, wherein the slots are positioned and configured to allow the distal member to flex as the inner shaft passes through the distal member.

11. An anchoring system, comprising:
an anchor including an anchor body and a distal member located at a distal end of the anchor body, the distal member having a suture receiving aperture; and
an implant delivery device, comprising:
a cannulated outer shaft, the cannulated outer shaft configured to engage a proximal end of the anchor body for driving the anchor into a bore; and
an inner shaft slidably received in the cannulated outer shaft, wherein a distal end of the inner shaft is extendable distally beyond a distal end section of the cannulated outer shaft such that, when the cannulated outer shaft is engaging the proximal end of the anchor body, the distal end of the inner shaft is extendable through the anchor body to engage a suture located within the suture receiving aperture, wherein the anchoring system is configured such that the suture can be tensioned at a location within the bore distal from the anchor body before the anchor body is implanted within the bore;
wherein the suture receiving aperture includes a slot in the distal member, wherein the slot is an L-shaped slot with an opening on a side of the distal member defining a first leg of the L-shaped slot and a longitudinally running slot in the distal member defining a second leg of the L-shaped slot, wherein a distal end of the distal member is closed and when the inner shaft is extended at least a portion of the inner shaft covers the opening on the side of the distal member so as to secure the suture within the distal member, wherein the anchoring system is configured such that the suture located in the suture receiving aperture is not driven distally beyond the distal member.

12. The anchoring system of claim 11, wherein the anchor body includes a threaded outer surface.

13. The anchoring system of claim 11, wherein the anchor body is cannulated, and the distal member at least partially enters the cannulated anchor body as the anchor body is driven into the bore over the distal member.

* * * * *